United States Patent [19]

Koslow et al.

[11] Patent Number: 5,792,513

[45] Date of Patent: Aug. 11, 1998

[54] CONTINUOUS SOLID STATE WEB COATING PROCESS

[75] Inventors: Evan E. Koslow, Weston; Richard D. Kendrick, Stratford; Gordon Spilkin, Stamford, all of Conn.

[73] Assignee: Koslow Technologies Corporation, Orange, Conn.

[21] Appl. No.: 813,055

[22] Filed: Mar. 7, 1997

[51] Int. Cl.⁶ .................. B05D 1/34; B05D 3/12
[52] U.S. Cl. .......... 427/195; 427/201; 427/365; 427/374.4; 427/375
[58] Field of Search ........... 427/180, 195, 427/201, 374.1, 374.4, 375, 389.9, 365, 366

[56] References Cited

U.S. PATENT DOCUMENTS

| | | | |
|---|---|---|---|
| 4,420,590 | 12/1983 | Gartner | 525/357 |
| 5,147,722 | 9/1992 | Koslow | 428/402 |
| 5,151,301 | 9/1992 | Kruger et al. | 427/294 |
| 5,225,242 | 7/1993 | Frankosky et al. | 427/209 |
| 5,360,419 | 11/1994 | Chen et al. | 604/374 |
| 5,413,747 | 5/1995 | Akers et al. | 264/211 |

Primary Examiner—Shrive Beck
Assistant Examiner—Fred J. Parker
Attorney, Agent, or Firm—Ware, Fressola, Van der Sluys & Adolphson LLP

[57] ABSTRACT

One or more particulate active agents are fused to the surface of a substrate web by mixing the particulate agents with a particulate binder having a particle size not exceeding an average diameter of approximately 40 microns and coating the composite mixture onto the surface of the substrate. Thereafter, the coated substrate is heated to a temperature equal to or greater than the Vicat softening temperature of the binder and compressed within the nip of a pair of pressure rolls to achieve fusion. If desired, a top layer may be placed upon the coated composite prior to the compression step. Also disclosed are various products manufactured by the process.

15 Claims, 1 Drawing Sheet

CONTINUOUS SOLID STATE WEB COATING PROCESS

TECHNICAL FIELD

This invention relates to a novel method for the continuous production of a web coated with a layer of a powdered active substance. The active substance is caused to adhere to the web by means of a thermoplastic binder present in a sufficiently small volume that it does not interfere with the adsorbent or otherwise desirable characteristics of the active material.

BACKGROUND ART

The closest known processes to that of this invention are described in Koslow U.S. Pat. Nos. 5,019,311; 5,147,722; 5,189,092; 5,249,948; and 5,331,037, their parent applications, their corresponding foreign patent applications and patents, and the references cited therein.

The above-mentioned patents disclose processes for the production of composite materials which are characterized by primary particles interconnected by a binder material. Some of these processes require high pressure and shear or extrusion through a die with carefully controlled back pressure. These prior art processes are extremely useful in producing a wide variety of articles including extruded solid forms such as activated carbon filters.

It would often be desirable to impregnate, cover, or otherwise treat a relatively fragile web base material with an active component such as a powdered adsorbent or absorbent material. One example would be a nonwoven medium coated with agents having water absorption and odor adsorption characteristics as in a diaper or hygiene product. A number of other related products will be apparent to those skilled in the art such as, for example, coated paper tissues and toweling, and fabrics such as surgical bandages and sanitary napkins. However, the fragile nature of the underlying base material would make it impractical to employ the known prior art techniques which require high pressure and shear.

In the prior art referred to above, the powdered active material is formed into a self-supporting structure by fusion of a thermoplastic material with which it is intimately mixed. However, the pressures, temperatures, and shear involved, or the process equipment used would not permit their application to fragile substrates such as the webs described herein. Accordingly, it is a primary object of the present invention to provide a method for continuously coating a relatively fragile web with a dry mixture of at least one particulate active material and a very finely divided particulate thermoplastic binder. Other objects, features, and advantages will become apparent from the following description and appended claims.

DISCLOSURE OF INVENTION

In accordance with the present invention a loose, dry composite powder is formed which comprises at least one group of particles of an active ingredient and particles of a thermoplastic binder. The binder particles are quite small in size, preferably on the order of 20 microns and no greater than approximately 40 microns on average. The particle size of the active ingredient may be much larger, within the range, for example, of 5–5000 microns. The small size of the thermoplastic binder particles causes them to adhere to the particles of the active ingredient by electrostatic and van der Waal forces. In addition to their tendency to stick to the active particles, the binder particles also have a high innate cohesion.

The mixture of active and binder powders is applied to the surface of a moving web by means of a knurled roller. The coated web, which can be preheated through a convective or infra-red oven, is then passed through the nip of a pair of rollers, one of which is heated, which apply both heat and pressure to fuse the thermoplastic binder to the active particles and to the underlying web. This step may also be employed to incorporate a second web to achieve a sandwich effect with the active material incorporated between two web surfaces. Upon leaving the heated rollers, the thermoplastic binder sets to form a single, composite structure.

BEST MODE FOR CARRYING OUT THE INVENTION

Figure 2:
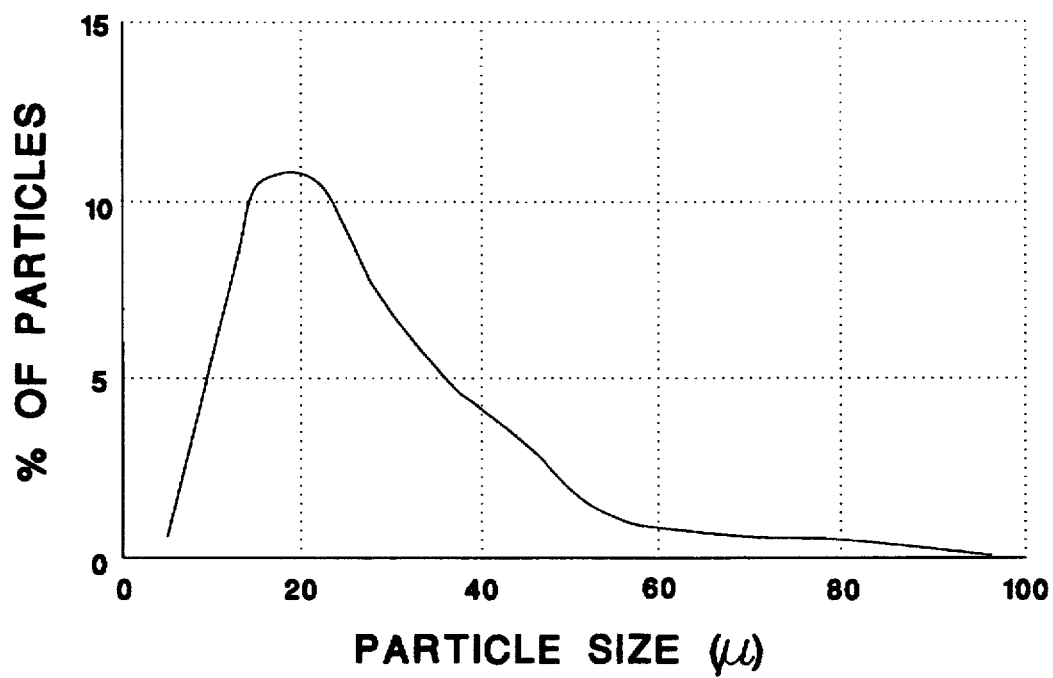
FIG. 2 is a graph showing the typical particle size distribution of a binder usable in this invention.

As has been described above, any of a large number of active particulate agents may be applied to an underlying web in accordance with this invention. Essentially the only limitation relates to the activity desired, e.g. liquid absorption, odor adsorption, medicament delivery, etc. The critical features of this invention, however, reside in the thermoplastic binder which is employed to coalesce the active particles and adhere them to the underlying web. For this purpose, the thermoplastic binder must be in the form of very small particles and must be present in a small enough volume that they do not interfere with the functioning of the active agent. Preferably, the binder will have an effective diameter of not more than 40 microns on average with an optimum size of 20 microns on average. A binder which is suitable for the process of this invention may be produced from normally solid, synthetic organic polymeric thermoplastic resins by the method disclosed in U.S. Pat. No. 3,432,483 of Peoples, et al. Examples of suitable binders are Microthene® F, microfine polyolefin powders produced by Quantum Chemical Company, such as, for example, their low density polyethylene designated FN-510 and their ethylene-vinyl acetate copolymer designated FE-532. FIG. 2 illustrates the typical particle size distribution of Microthene FN-510 powder.

Figure 1:
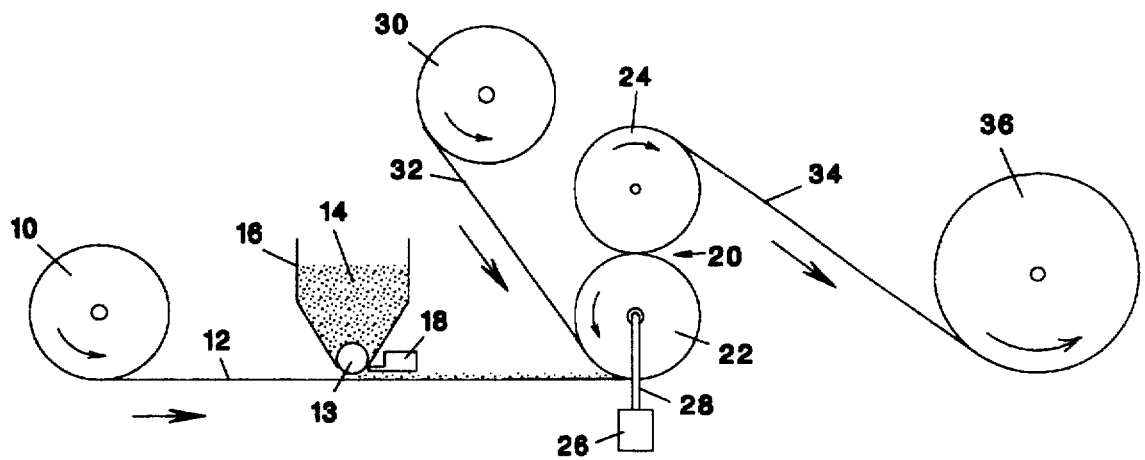
FIG. 1 is a schematic diagram illustrating an apparatus for the practice of the method of this invention.

FIG. 1 illustrates an exemplary apparatus for the practice of this invention. A supply roll 10 provides a web 12 of the substrate to be treated, such as a nonwoven tissue or towelling paper. Downstream from supply roll 10 is a knurled roller 13 positioned to receive the composite powder 14 of this invention from a hopper 16 and apply the powder to the upper surface of the web 12. The surface of the knurled roller 13 may be designed to provide a substantially continuous coating or, alternatively, a coating of a specific design such as, for example, stripes on the web surface. A brush 18 may be employed to aid in removing the composite powder from the knurled roller 13. Thereafter, the web 12 is passed through the nip 20 between a heated idler roller 22 and a drive roller 24. A pneumatic cylinder 26 is connected via a rod 28 to the axle of the idler roller 22 to maintain a desired pressure on the web within the nip 20. In passing over the surface of the heated roller 22, the binder is heated to a temperature equal to or greater than its Vicat softening temperature as it enters the nip 20. Within this nip the binder material fuses under pressure with the active material and with the material of the web. In the illustrated apparatus there is provided a second supply roll 30 of a web 32 which may be of the same or a different material from that of base web 12. This web is also passed between the nip 20 of the rollers 22, 24 and on the top of the particulate material which is being fused. Accordingly, the web 34 which leaves the roller 24 is a composite with both a top and bottom sheet, film, or nonwoven layer. Upon leaving the nip 20, the binder cools and hardens, thereby forming the desired composite. The composite web 34 passes onto a takeup roll 36. Some specific examples of the process of this invention are as follows.

Note: The Vicat softening temperature is defined by Quantum Chemical Company, Cincinnati, Ohio, as "... the temperature at which the finished |thermoplastic| article becomes too soft to withstand stresses and keep its shape. It is the temperature at which a flat-ended needle of 1 mm cross section under a load of 1 kg penetrates 1 mm into a ... specimen. In the Vicat test, the temperature of the specimen is increased at a uniform rate."

EXAMPLE 1
Iodine Paper

Iodine paper has utility when used, for example, in a filter unit as a germicidal element.

Both the substrate and the upper layer were 23 cm wide webs of 0.8 oz./sq. yd.spun bonded polyester identified as REEMAY type 2016. The production apparatus is as generally shown in FIG. 1 and described above.

The powder mixture consisted of 10% by weight ethylene-vinyl acetate copolymer, (FE532 of Quantum Chemical Company, Cincinnati, Ohio) and 90% by weight iodinated ion exchange resin, 47.5% iodine, balance inert, approximately 20–50 mesh particle size (Grade A605 PURADINE™ iodinated resin from The Purolite Company, Bala Cynwyd, Pa.).

The webs moved at the rate of 0.6 m/min and the composite powder was laid down in the amount of 0.02–0.07 g/cm². The heated roller was 10 inches in diameter and heated by hot oil to a temperature of 135° C. The binder reached its Vicat softening temperature of 75°–80° C. in the nip. Pressure in the nip was maintained at approximately 70 kg/cm. The product was a composite medium of good strength and porosity containing nearly 85% by weight of iodated resin. The fact that the resin is not dry prior to processing did not have a significant impact on the quality of the product.

EXAMPLE 2
Carbon/Soda Paper.

Carbon and sodium-bicarbonate impregnated paper has particular utility as an odor removing component in, for example, an odor adsorbing sheet used in air filtration applications.

The apparatus was substantially identical to that of Example 1. However, the composite powder comprised 17% FE-532. The remaining 83% was 50% 80–325 mesh (500–44 μ) activated carbon and 50% 30–40 μ particles of sodium bicarbonate (NaHCO₃). The web was run at a speed of 0.6–0.9 m/min and powder was deposited at the rate of 0.015 g/cm². The heated roller was at a temperature of 138° C. Three impregnated papers having the same widths as in Example 1 were successfully obtained with (i) both the upper and lower substrates consisting of cellulosic tissue, (ii) both the upper and lower substrates consisting of cellulosic towel stock, and (iii) the lower substrate consisting of cellulosic towel stock and the upper substrate layer consisting of cellulosic tissue stock.

EXAMPLE 3
Carbon Air or Liquid Filter Paper

This adsorbent medium has utility in any situation where carbon treatment of either air or liquid is desirable.

The apparatus was similar to that of Example 1. The lower and upper substrates were both spun bonded polypropylene, (TYPAR grade 135 of Reemay Corporation). The powder mixture was 30% by weight FE-532 and 70% coconut carbon of 80–325 mesh (500–44 μ). The heated drum was at a temperature of 150° C. and the web speed was 0.6–1.0 m/min. The composite powder was deposited in the amount of 0.015 g/cm². This adsorbent medium was suitable for air filtration. The process was repeated substituting a bituminous coal based carbon for the coconut carbon. The resulting composite medium was optimal for water filtration applications. Both materials were entirely stable when operated in water and did not release fines.

EXAMPLE 4
Manganese Oxide Paper

This paper has utility as a filter for removal of heavy metals, such as lead.

The apparatus was substantially identical to that of the preceding examples. Both the lower substrate and the upper layer comprised 25 cm wide CASTLE® facing spun bonded polypropylene from Kimberly-Clark Corporation. The powder mixture was 17% FE-532 and 83% MnO₂ of average particle size approximately 44 μ. Web speed was 0.8–1.5 m/min. Powder lay-down was 0.015 g/cm² and the heated drum temperature was 135° C. The resulting composite medium retains the manganese dioxide in its fully active state where it is capable of oxidizing and precipitating lead, cadmium and other heavy metals.

EXAMPLE 5
Super-Absorbent Composite.

This product has utility in absorbing liquids and might be used, for example, in diapers.

The apparatus was similar to those described in the preceding examples. Both the lower substrate and the upper layer comprised spun bonded polypropylene from Kimberly-Clark Corporation. The powder mixture was 10% FE-532 and 90% FavorSorb® 880 (a super absorbent acrylic-based polymer obtained from Stockhausen Corporation, Greensboro, N.C. Two runs were made as follows, with production of suitable, super-absorbent composites:

(a) The composite powder laydown was 0.015 g/cm². Web speed was 0.8 m/min, the temperature of the heated drum was 138° C., and pressure was approximately 100 psi.

(b) The composite powder laydown was 0.36 g/cm². Web speed was 0.5–0.6 m/min, the temperature of the heated drum was 177° C., and pressure was approximately 100 psi.

This produced a composite medium having excellent water absorption characteristics.

It is believed that the many advantages of this invention will now be apparent to those skilled in the art. It will also be apparent that a number of variations and modifications may be made therein without departing from its spirit and scope. Accordingly, the foregoing description is to be construed as illustrative only, rather than limiting. This invention is limited only by the scope of the following claims.

We claim:

1. A process for coating the surface of a substrate web with an active agent and a binder which comprises:
   preparing a mixture of at least one particulate active agent and a particulate binder material having an average particle size not exceeding approximately 40 microns;
   applying the mixture to said substrate web to produce a uniform or textured surface of powder covering the substrate web;
   heating the powder to at least the Vicat softening temperature of said binder material but below the melting temperature of the substrate web and said active agent; and
   thereafter applying pressure to said substrate web to cause the softened binder material to fuse said particulate active agent particles to each other and to said substrate web to form a surface coated substrate web.

2. The process of claim 1 comprising the additional step, prior to said heating step, of depositing upon said mixture an upper layer of sheet material, to simultaneously subject said substrate web, powder mixture, and upper layer to said application of pressure.

3. The process of claim 1 wherein said pressure is applied by passing the substrate web through the nip of a pair of pressure rollers.

4. The process of claim 2 wherein said pressure is applied by passing the substrate web and upper layer through the nip of a pair of pressure rollers.

5. The process of claim 1 wherein said binder material is a synthetic organic polymeric thermoplastic resin.

6. The process of claim 5 wherein said binder material is ethylene-vinyl acetate copolymer.

7. The process of claim 5 wherein said resin is polyethylene.

8. The process of claim 7 wherein said resin is low density polyethylene.

9. The process of claim 7 wherein said resin is high density polyethylene.

10. The process of claim 1 wherein said active agent is carbon.

11. The process of claim 1 wherein said active agent is sodium bicarbonate.

12. The process of claim 11 wherein said active agent comprises activated carbon.

13. The process of claim 1 wherein said active agent is iodated resin.

14. The process of claim 1 wherein said active agent is manganese dioxide.

15. The process of claim 1 wherein said active agent is a liquid absorbent.

* * * * *